Figure 1:
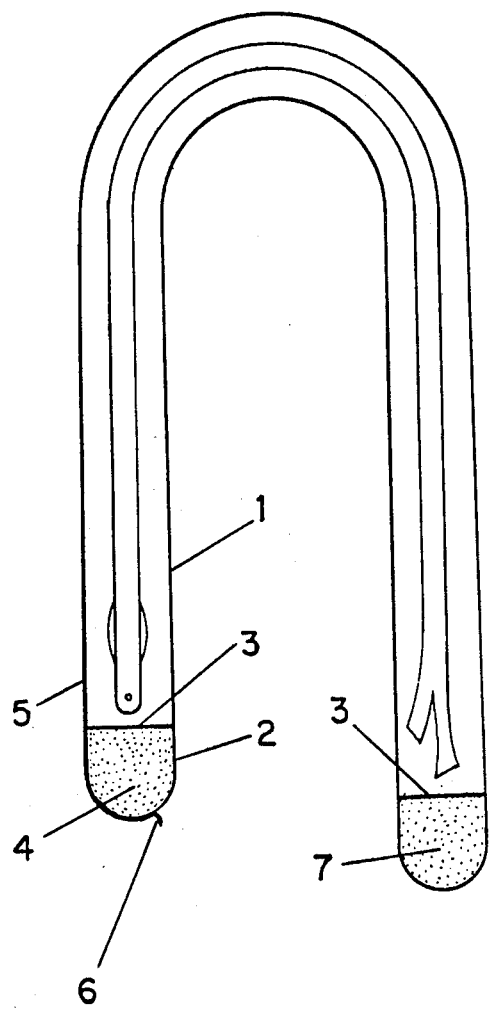

United States Patent [19]

Uson

[11] 4,269,310
[45] May 26, 1981

[54] ASEPTIC CONTAINER AND MANIPULATOR FOR A URETHRAL CATHETER HAVING AN INTEGRAL ANTISEPTIC SOLUTION AND LUBRICANT

[76] Inventor: Aurelio C. Uson, Valle Del Moro No. 45, Las Lomos, Boadilla Del Monte, Madrid, Spain

[21] Appl. No.: 38,558

[22] Filed: May 14, 1979

[51] Int. Cl.$^3$ ............... A61B 19/02; A61M 25/00; B65D 85/00
[52] U.S. Cl. ............... 206/210; 206/364; 128/349 R
[58] Field of Search ............... 206/210, 364, 63.3; 128/349 R

[56] References Cited

U.S. PATENT DOCUMENTS

| 2,808,927 | 10/1957 | Utley et al. | 206/63.3 |
| 3,338,401 | 8/1967 | Regan, Jr. | 206/63.3 |
| 3,648,704 | 3/1972 | Jackson | 206/364 |
| 3,854,483 | 12/1974 | Powers | 206/364 |
| 3,967,728 | 7/1976 | Gordon et al. | 206/210 |

Primary Examiner—William T. Dixson, Jr.
Attorney, Agent, or Firm—Anthony J. Casella

[57] ABSTRACT

An aseptic container and manipulator for urethral catheters comprising an elongated tubular container for the catheter, and having at one end a first enclosure containing a lubricant while at the other end there is a second enclosure having an antiseptic solution therein, with the wall between said container and the first enclosure being frangible. By this arrangement the first enclosure may be opened and the frangible wall thereof pierced, and the catheter may be inserted into the patient by manipulating the outer sleeve of the container, without the physician requiring sterile gloves, forceps or other instruments.

2 Claims, 2 Drawing Figures

U.S. Patent

May 26, 1981

4,269,310

ASEPTIC CONTAINER AND MANIPULATOR FOR A URETHRAL CATHETER HAVING AN INTEGRAL ANTISEPTIC SOLUTION AND LUBRICANT

The subject invention deals with the development of a container made of any suitable material for keeping sterile urethral or ureteral catheters, and at the same time allowing for necessary antiseptic solution, as well as lubricant, for quick and safe urethal catheterization in both men or women, as well as in children.

A uretheral or urethral catheter is usually presented in a container made of a plastic material which is steriized. However, when it is going to be used, the catheter has to be removed from its sheath or container, and in order to be introduced aseptically into the urethra and bladder of the patient, the catheter must be handled by the physician with gloved hands or by using special clamps or forceps. In addition, the urethral meatus, as well as the glans penis in men, or the introitus in women, must be cleaned properly with an antiseptic solution, and finally the tip of the Foley catheter or any other urethral catheter must be lubricated with a lubricant.

All of this entails a procedure which is time-consuming and cumbersome, since the lubricant, the antiseptic solution, the gloves, or any necessary instrument may not be readily available for a quick, safe and aseptic catheterization.

For these reasons, the subject invention provides an aseptic container for urethral and ureteral catheters which need to be introduced in an aseptic manner, allowing a direct manipulation, by holding the urethral catheter within its sleeve or container and passing it into the urethra without any additional requisite or waste of time.

Figure 2:
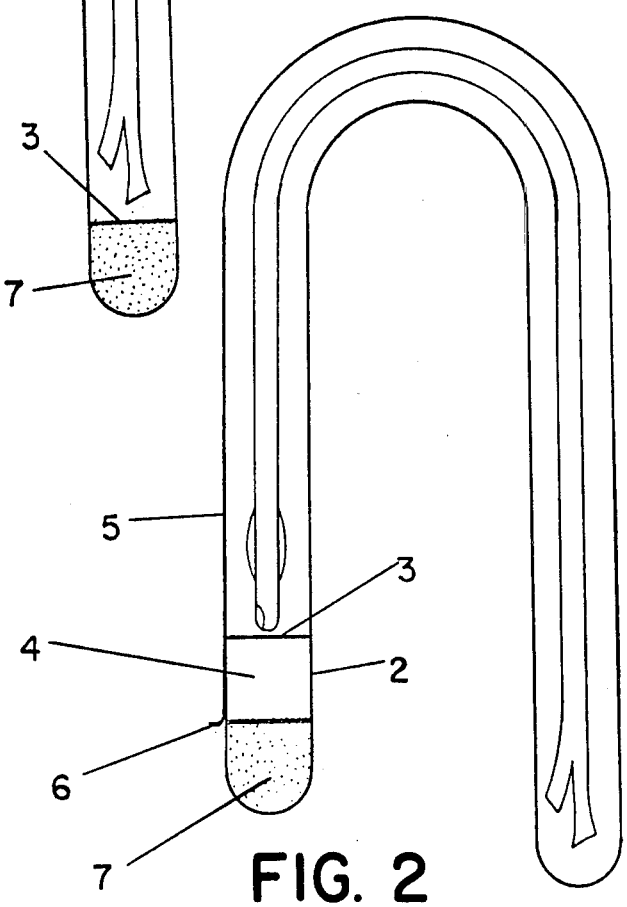

In the accompanying drawings, FIGS. 1 and 2 are shown the container and within it the urethral catheter as well as the compartments for the lubricant and the antiseptic solution.

The container 1, which shape and size will adapt itself to any variation to fit properly, any urethral or ureteral catheter, includes in one end an enclosure 2, which is separated by a wall 3 which is fragile. Within the enclosure the lubricant 4 is provided, so that when the catheter is being used, the catheter will pass through the enclosure 2, and thus will be progressively lubricated.

The container and aseptic manipulator for urethral and other types of catheter, in addition to the aforementioned elements in the preceding paragraph, it can have another enclosure 7, which consists of an hermetically sealed envelope, containing a small towel or sponge impregnated with antiseptic solution for sterilization of the glans, vaginal introitus and urethral meatus, as shown in FIG. 2.

As it can be observed in the same figure, the container includes along one of its longitudinal sides 5, a tear strip 6 which can be detached easily from the container thereby leaving the end of the container freely opened.

At such time the physician by merely grasping the sleeve-like container 1, without the use of gloves may readily and quickly insert the catheter into the urethral channel, whereby the subject invention simultaneously functions as both a container as well as a manipulator.

Although the invention has been described with respect to several preferred embodiments thereof, it is readily apparent that variations, modifcations and alterations may be made therein without departing from the spirit and scope of the invention. As an example, in lieu of using a tear strip 6, the enclosure 2 may be fully sealed and the fragile wall 3 may be readily broken by squeezing of the enclosure 2 such that lubricant 4 passes through the broken wall 3 and lubricates the tip of the catheter. Still further, the elongated container 1 including the end closure which contain the lubricant and antiseptic may be made of double wall thickness for greater strength and protection, with the outer sleeve being first removed preparatory to the aseptic introduction of the catheter as described above. It is noted that in the embodiment of FIG. 1, the enclosure 2 is disposed at one end of the elongated container and manipulator 1 while the antiseptic solution 7 is disposed at the opposite end thereof. In the embodiment of FIG. 2, both of the enclosures for the lubricant and antiseptic solution are disposed at one end of the container and manipulator.

What is claimed is:

1. Aseptic container and manipulator for urethral catheters providing lubricant and antiseptic, characterized by having at one end an enclosure which is separated from the main container by a fragile wall element which is disposed transversely to the length of the container; a lubricant contained within said enclosure; a tear strip disposed in a longitudinal side of the container for releasing the lubricant of the enclosure and opening the container; and including a second enclosure having an antiseptic solution therein, said second enclosure located in one end or the other of the container.

2. Aseptic container and manipulator for urethral catheters providing lubricant and antiseptic, as in claim 1 characterized by said container being sufficiently flexible whereby the catheter may be forced out of the container and through said enclosure having the lubricant therein so as to progressively lubricate the catheter to facilitate the passage thereof into the urethera without requiring the use of sterile gloves, forceps, or any other instruments.

* * * * *